United States Patent [19]

Knickmeyer et al.

[11] 4,271,311

[45] Jun. 2, 1981

[54] ESTERIFICATION OF PHENOL CATALYZED WITH A STRONG BASE PLUS BORON

[75] Inventors: William W. Knickmeyer, Aurora; James Spanswick, Wheaton; James R. Stephens, Naperville, all of Ill.

[73] Assignee: Standard Oil Company (Indiana), Chicago, Ill.

[21] Appl. No.: 57,198

[22] Filed: Jul. 13, 1979

[51] Int. Cl.$^3$ ............... C07C 69/773; C07C 69/355; C07C 69/035

[52] U.S. Cl. .................... 560/86; 260/410.5; 560/100; 560/102; 560/109; 560/130; 560/146

[58] Field of Search ............... 560/86, 100, 102, 109

[56] References Cited

U.S. PATENT DOCUMENTS

| | | | |
|---|---|---|---|
| 3,617,226 | 11/1971 | List et al. | 560/86 |
| 3,772,389 | 11/1973 | Lowrance | 560/86 |
| 3,784,578 | 1/1974 | Swodenk et al. | 560/100 |

Primary Examiner—Joseph E. Evans
Attorney, Agent, or Firm—William H. Magidson; William T. McClain

[57] ABSTRACT

Esterification of phenolic compounds which comprises reacting a phenolic compound and a carboxylic acid using a catalyst consisting essentially of an alkali metal compound and a boron compound wherein said alkali metal compound is at least one member selected from the group consisting of alkali metal salts of boric acid, alkali metal polyborates, alkali metal hydroxides, and alkali metal borohydrides and said boron compound is at least one member selected from the group consisting of boric acid, boric anhydride, alkali metal polyborates, alkali metal salts of boric acid and alkali metal borohydrides.

8 Claims, No Drawings

ESTERIFICATION OF PHENOL CATALYZED WITH A STRONG BASE PLUS BORON

BACKGROUND OF THE INVENTION

1. Field of the Invention

This invention relates to the esterification of phenolic compounds using a catalyst consisting essentially of an alkali metal compound and a boron-containing compound. More particularly, this invention relates to the production of diphenyl esters of aromatic nonvicinal benzene dicarboxylic acids using a catalyst consisting essentially of an alkali metal compound and a boron compound wherein said alkali metal compound is at least one member selected from the group consisting of alkali metal salts of boric acid, alkali metal polyborates, alkali metal hydroxides, and alkali metal borohydrides and said boron compound is at least one member selected from the group consisting of boric acid, boric anhydride, alkali metal polyborates, alkali metal salts of boric acid and alkali metal borohydrides.

Lowrance in U.S. Pat. No. 3,772,389 discloses that prior to his invention it was impossible to form phenyl esters directly from the corresponding phenolic compound and carboxylic acids and that the synthesis required the use of the corresponding carboxylic acid chloride. Lowrance discloses that the direct esterification can be carried out using a catalytic amount of a borate-sulfuric acid complex at a suitable temperature and for a suitable time. Examples 1 and 2 of Lowrance indicate that esterification is impossible using sulfuric acid alone or boric acid alone as the catalyst, while Examples 4–7 illustrate that the boric acid sulfuric acid catalyst system cannot be replaced with zinc chloride, p-toluene sulfonic acid, boron trifluoride, or phosphoric acid. All of the examples of Lowrance employ a diluent to facilitate removal of water from the reaction vessel and force the esterification to substantial completion. It appears from Example 3 of Lowrance that yields are approximately 94% when a monocarboxylic acid is reacted with a phenolic compound.

While Lowrance's process appears to be an advance in the art, the Lowrance process has certain drawbacks, particularly the use of diluents for carrying out the reaction. Further, nonvicinal benzene dicarboxylic acids are harder to esterify than benzene monocarboxylic acids. This is unfortunate since the phenyl esters of nonvicinal dicarboxylic acids are potentially useful intermediates for the production of the so-called polyarylates, i.e., ester interchange reaction products of phenyl esters of nonvicinal benzene dicarboxylic acids and aromatic polyhydric alcohols such as Bisphenol A, etc. Accordingly, there is a need for additional catalyst systems for the production of esters of phenolic compounds.

The general object of this invention is to provide a new process for the production of phenolic esters of carboxylic acids. A more specific object of this invention is to provide a new process for the production of diphenyl esters of nonvicinal benzene dicarboxylic acids. Other objects appear hereinafter.

We have now found that the objects of this invention can be attained by reacting a phenolic compound with a carboxylic acid using a catalyst composition consisting essentially of an alkali metal compound and a boron compound wherein said alkali metal compound is at least one member selected from the group consisting of alkali metal salts of boric acid, alkali metal polyborates, alkali metal hydroxides, and alkali metal borohydrides and said boron compound is at least one member selected from the group consisting of boric acid, boric anhydride, alkali metal polyborates, alkali metal salts of boric acid and alkali metal borohydrides. Surprisingly, these catalysts are more effective than the borate-sulfuric acid complexes of Lowrance. Both the alkali metal component and boron component are essential. For example, manganese borate and zinc borate cannot be used in place of the alkali metal component and boron component.

SUMMARY OF THE INVENTION

Briefly, this invention comprises reacting a phenolic compound and organic carboxylic acid, preferably neat, with a phenolic compound in the presence of a catalyst composition consisting essentially of an alkali metal compound and a boron compound wherein said alkali metal compound is at least one member selected from the group consisting of alkali metal salts of boric acid, alkali metal polyborates, alkali metal hydroxides, and alkali metal borohydrides and said boron compound is at least one member selected from the group consisting of boric acid, boric anhydride, alkali metal polyborates, alkali metal salts of boric acid and alkali metal borohydrides.

Any of the phenolic compounds useful in Lowrance, which is incorporated by reference, containing at least one hydrogen atom on the benzene ring ortho to the OH moiety of the phenolic compound can be used. Suitable phenolic compounds include phenol, paracresol, etc. As indicated above, phenol is the preferred phenolic compound since it can be used to produce the diphenyl esters of nonvicinal benzene dicarboxylic acids which are then useful for the production of polyarylates.

Suitable carboxylic acids useful in this invention include aliphatic carboxylic acids containing from 2 to 18 carbon atoms, such as acetic acid, propionic acid, lauric acid, stearic acid, etc.; aliphatic dicarboxylic acids, such as succinic acid, glutaric acid, sebacic acid; aromatic carboxylic acids, such as benzoic acid, toluic acid, chlorobenzoic acid, naphthoic acid, isophthalic acid, terephthalic acid, 2,6-naphthalene dicarboxylic acid; 2,2',6,6'-tetramethylbiphenyl-4,4' dicarboxylic acid, and trimellitic acid, as well as any of the organic carboxylic acids suitable for use in Lowrance, which is incorporated by reference.

The alkali metal compounds useful in this invention include sodium hydroxide, potassium hydroxide, lithium hydroxide, sodium borohydride, sodium metaborate, potassium metaborate, sodium orthoborate, potassium metaborate, sodium salt of polyboric acids, etc. Suitable boron compounds include sodium borohydride, boric acid, boric anhydride, sodium orthoborate, potassium orthoborate, potassium borate, potassium orthoborate, potassium salts of polyboric acid, sodium salts of polyboric acid, etc. In general, the concentration of alkali metal compound to boron compound can be in the range of about 1:20 equivalents to 20:1 equivalents. However, substantially stoichiometric concentrations in the range of 2:1 to 1:3 are preferred. Each of the catalyst components can be present in a concentration from about 0.001 to 2.0 moles of catalyst per mole of phenolic compound. The optimum concentration can be determined by routine experimentation.

While various inert diluents can be used in the process, it is generally preferred to operate neat and use a sufficient excess of phenolic compound to form a melt for dissolution of the carboxylic acid, particularly the nonvicinal benzene dicarboxylic acids. Accordingly, phenolic compound can be used in a concentration of about 1 to 20 equivalent of phenolic compound per equivalent of carboxylic acid.

In somewhat greater detail the process of this invention can be carried out at a temperature of about 50° C., preferably 270° C. to approximately 400° C., the minimum temperature being preferably sufficiently high to provide the phenolic compound in a molten form.

As is well recognized, the higher the reaction temperature, the faster the rate of reaction and the more rapid the rate of water removal. Further, the reaction can be carried out at atmospheric pressure, under vacuum, or under pressure, if desired.

EXAMPLE 1

One hundred grams terephthalic acid, 100 grams isophthalic acid, 500 grams phenol and the concentration of catalyst indicated in Table I below, was added to a 1-liter Paar reactor fitted with a 2-blade, air driven turbine stirrer, thermocouple, oil-filled pressure gauge, nitrogen inlet, baffles and a needle valve leading to a condenser. The reactor was closed, flushed with nitrogen, sealed and heated with stirring to 300°–320° C., generating a pressure of 180 psi. When the reactor reached 300° C., a mixture of phenol and water was vented from the reactor through the needle valve at a rate sufficient so that the condensate just remained cloudy in the condenser. Venting was continued throughout the 3–4 hour period required for the pressure to gradually drop to about 25 to 50 psi. The condensate was collected after each ½ hour period and analyzed by Karl Fischer water analysis to determine the weight of water evolved. The total concentration of water evolved is set forth below in Table I.

TABLE I

| Catalyst | Milliliters Water Evolved |
|---|---|
| None | 24.1 |
| 0.2g NaOH | 23.6 |
| 0.2g NaBH$_4$ | 39.7 |
| 0.2g NaOH/0.3g H$_3$BO$_3$ | 36.8 |
| 1.375g Na$_2$B$_4$O$_7$ . 10H$_2$O | 32.7 |
| 1.9g Na$_2$B$_2$O$_4$ . 8H$_2$O | 34.5 |

The above data clearly shows that the catalysts of this invention comprising an alkali metal compound and a boron compound are effective catalysts for the esterification of carboxylic acids with phenolics.

EXAMPLE 2

Example 1 was repeated in a reactor system similar to that described in Example 1, except that the needle valve fitted directly to the reactor head was removed and replaced by a fractionating column twelve inches long and one inch in diameter packed with glass helicies. The top of the column was fitted with a needle valve and the rate of distillation at the top of the column was approximately 1.5 ml./min. The catalyst and milliliters of water evolved are set forth below in Table II.

TABLE II

| Catalyst | Milliliters Water Evolved |
|---|---|
| None | 37.83 |
| 0.1 ml H$_2$SO$_4$/0.3g H$_3$BO$_3$ | 38.7 |
| 0.5 Na$_2$SO$_4$ | 34.07 |
| 0.2g NaOH/0.3g H$_3$BO$_3$ | 45.6* |

*43.37 ml = 100% theoretical conversion

The above data clearly shows that the alkali metal/boron system of this invention is a more effective catalyst than the sulfuric acid/borate system of the Lowrance patent. G.C. analysis of the NaOH/0.3gH$_3$BO$_3$ catalyzed esterification indicated that there was 99% diester formed.

Essentially the same results can be attained by replacing the nonvicinal benzene dicarboxylic acids with aliphatic carboxylic acids such as acetic acid, succinic acid, or aromatic acids such as benzoic acid and trimellitic acid. Essentially the same result can be attained by replacing phenol with cresol.

We claim:

1. The process of esterification of phenolic compounds which comprises reacting a phenolic compound and an aromatic carboxylic acid using a catalyst consisting essentially of an alkali metal compound and a boron compound wherein said alkali metal compound is at least one member selected from the group consisting of alkali metal salts of boric acid, alkali metal polyborates, alkali metal hydroxides, and alkali metal borohydrides and said boron compound is at least one member selected from the group consisting of boric acid, boric anhydride, alkali metal polyborates, alkali metal salts of boric acid and alkali metal borohydrides.

2. The process of claim 1 wherein said phenolic compound comprises phenol.

3. The process of claim 2 wherein said carboxylic acid comprises a nonvicinal benzene dicarboxylic acid.

4. The process of claim 1 wherein said carboxylic acid comprises a nonvicinal benzene dicarboxylic acid.

5. The process of claim 1 wherein said carboxylic acid comprises a mixture of isophthalic acid and terephthalic acid.

6. The process of claim 1 wherein said reaction is carried out neat.

7. The process of claim 1 wherein said alkali metal compound and said boron compound comprises an alkali metal borohydride.

8. The process of claim 1 wherein said reaction is carried out at 270° C. to 400° C.

* * * * *